United States Patent
Smith

(10) Patent No.: US 7,720,622 B2
(45) Date of Patent: May 18, 2010

(54) NON-DESTRUCTIVE SYSTEMS, DEVICES, AND METHODS FOR EVALUATING IONTOPHORESIS DRUG DELIVERY DEVICES

(75) Inventor: Gregory A. Smith, Issaquah, WA (US)

(73) Assignee: TTI ellebeau, Inc., Tokyo (JP)

( * ) Notice: Subject to any disclaimer, the term of this patent is extended or adjusted under 35 U.S.C. 154(b) by 330 days.

(21) Appl. No.: 11/850,602

(22) Filed: Sep. 5, 2007

(65) Prior Publication Data

US 2008/0058756 A1    Mar. 6, 2008

Related U.S. Application Data

(60) Provisional application No. 60/842,445, filed on Sep. 5, 2006.

(51) Int. Cl.
G06F 11/30 (2006.01)

(52) U.S. Cl. .................... 702/65; 702/182; 604/20

(58) Field of Classification Search .............. 702/64, 702/65; 604/20, 65
See application file for complete search history.

(56) References Cited

U.S. PATENT DOCUMENTS

| | | | |
|---|---|---|---|
| 5,395,310 A | 3/1995 | Untereker et al. | 604/20 |
| 5,582,586 A | 12/1996 | Tachibana et al. | 604/20 |
| 6,245,057 B1 | 6/2001 | Sieben et al. | 604/891.1 |
| 6,391,015 B1 | 5/2002 | Millot | 604/503 |
| 6,692,456 B1 | 2/2004 | Eppstein et al. | 604/22 |
| 6,928,318 B2 | 8/2005 | Simon | 604/20 |
| 6,939,311 B2 | 9/2005 | Geiger | 600/573 |
| 7,018,345 B2 | 3/2006 | Mori et al. | 600/573 |
| 2003/0088205 A1 | 5/2003 | Chandrasekaran et al. | 604/20 |
| 2004/0087671 A1 | 5/2004 | Tamada et al. | 516/99 |
| 2004/0236268 A1 | 11/2004 | Mitragotri et al. | |
| 2005/0267440 A1 | 12/2005 | Herman et al. | 604/501 |
| 2006/0031035 A1 | 2/2006 | Brott et al. | |
| 2006/0095001 A1 | 5/2006 | Matsumura et al. | 604/20 |
| 2006/0116628 A1 | 6/2006 | Matsumura et al. | 604/20 |
| 2006/0129085 A1 | 6/2006 | Tanioka et al. | 604/20 |
| 2006/0135906 A1 | 6/2006 | Matsumura et al. | 604/20 |
| 2006/0173401 A1 | 8/2006 | Tanioka et al. | 604/20 |
| 2006/0286102 A1 | 12/2006 | Jin et al. | 424/143.1 |
| 2008/0208106 A1 | 8/2008 | Kogure et al. | 604/20 |

FOREIGN PATENT DOCUMENTS

EP    0 904 801 A2    3/1999

(Continued)

OTHER PUBLICATIONS

Hirvonen, J., et al., "Experimental Verification of the Mechanistic Model for Transdermal Transport Including Iontophoresis," *J. Controlled Release*, 56:169-174, 1998.

(Continued)

*Primary Examiner*—Manuel L Barbee
(74) *Attorney, Agent, or Firm*—Seed IP Law Group PLLC

(57) ABSTRACT

Systems, devices, and methods for evaluating iontophoresis devices. An impedance spectrometer is operable to determine an impedance of an iontophoresis device and a controller configured to perform a comparison of the measured impedance of the iontophoresis device to stored reference data, and to generate a response based in part on the comparison.

18 Claims, 4 Drawing Sheets

FOREIGN PATENT DOCUMENTS

| | | |
|---|---|---|
| EP | 904801 A2 * | 3/1999 |
| EP | 0 931 564 A1 | 7/1999 |
| EP | 1 440 707 A1 | 7/2004 |
| JP | 06-070987 | 3/1994 |
| JP | 3-40517 | 3/2000 |
| JP | 2000-229128 | 8/2000 |
| JP | 2000-229129 | 8/2000 |
| JP | 2000-237326 | 9/2000 |
| JP | 2000-237327 | 9/2000 |
| JP | 2000-237328 | 9/2000 |
| JP | 2000-237329 | 9/2000 |
| JP | 2000-288097 | 10/2000 |
| JP | 2000-288098 | 10/2000 |
| JP | 2001-120670 | 5/2001 |
| JP | 2001-523996 | 11/2001 |
| JP | 2004-024699 | 1/2004 |
| JP | 2004-317317 | 10/2004 |
| JP | 2004-357313 | 12/2004 |
| JP | 2006-149891 | 6/2006 |
| JP | 2006-212194 | 8/2006 |
| JP | 2006-262943 | 10/2006 |
| WO | WO 03/037425 | 5/2003 |
| WO | 2006/055729 | 5/2006 |
| WO | 2007/010900 | 1/2007 |
| WO | 2007/041115 A1 | 4/2007 |
| WO | 2008/027218 | 3/2008 |

OTHER PUBLICATIONS

Krämer, S., "Absorption Prediction from Physicochemical Parameters," *Pharm Sci Technolo Today*, 2(9):373-380, Sep. 1999.

U.S. Appl. No. 11/850,597, filed Sep. 5, 2007, Smith.

U.S. Appl. No. 60/627,952, filed Nov. 16, 2004, Matsumura et al.

U.S. Appl. No. 60/842,445, filed Sep. 5, 2006, Smith.

Asher, S., et al., "Photonic Crystal Carbohydrate Sensors: Low Ionic Strength Sugar Sensing," *J. Am. Chem. Soc.*, 125(11), 3322-3329, 2003.

JCAAI.org, "Diagnostic Tests of Cell Mediated Immune Reactions (Delayed Hypersensitivity)," *Ann Allergy*, 75:543-625, 1995. URL—http://www.jcaai.org//pp/adt_3-02.asp, retrieved Aug. 23, 2007, 2 pages.

Merclin, N., "Electrochemical Methods for Drug Characterisation and Transdermal Delivery," *Uppsala universitet, doktorsavhandling*, 2003.

* cited by examiner

NON-DESTRUCTIVE SYSTEMS, DEVICES, AND METHODS FOR EVALUATING IONTOPHORESIS DRUG DELIVERY DEVICES

CROSS-REFERENCE TO RELATED APPLICATION

This application claims the benefit under 35 U.S.C. §119(e) of U.S. Provisional Patent Application No. 60/842,445 filed Sep. 5, 2006, the content of which is incorporated herein by reference in its entirety.

BACKGROUND

1. Field

The present disclosure generally relates to the field of iontophoresis and, more particularly, to systems, devices, and methods for evaluating iontophoresis drug delivery devices.

2. Description of the Related Art

Iontophoresis employs an electromotive force and/or current to transfer an active agent (e.g., a charged substance, an ionized compound, an ionic drug, a therapeutic, a bioactive-agent, and the like), to a biological interface (e.g., skin, mucus membrane, and the like), by using a small electrical charge applied to an iontophoretic chamber containing a similarly charged active agent and its vehicle.

Iontophoresis devices typically include an active electrode assembly and a counter electrode assembly, each coupled to opposite poles or terminals of a power source, for example a chemical battery. Each electrode assembly typically includes a respective electrode element to apply an electromotive force and/or current. Such electrode elements often comprise a sacrificial element or compound, for example silver or silver chloride.

The active agent may be either cationic or anionic, and the power source may be configured to apply the appropriate voltage polarity based on the polarity of the active agent. Iontophoresis may be advantageously used to enhance or control the delivery rate of the active agent. The active agent may be stored in a reservoir such as a cavity. See e.g., U.S. Pat. No. 5,395,310. Alternatively, the active agent may be stored in a reservoir such as a porous structure or a gel. An ion exchange membrane may be positioned to serve as a polarity selective barrier between the active agent reservoir and the biological interface. The membrane, typically only permeable with respect to one particular type of ion (e.g., a charged active agent), prevents the back flux of oppositely charged ions from the skin or mucous membrane.

Commercial acceptance of iontophoresis devices is dependent on a variety of factors, such as cost to manufacture, shelf life, stability during storage, efficiency and/or timeliness of active agent delivery, biological capability, and/or disposal issues. Commercial acceptance of iontophoresis devices is also dependent on their reliability and performance. Therefore, it may be desirable to have novel approaches for verifying the quality and/or integrity of iontophoresis devices during manufacturing.

The present disclosure is directed to overcoming one or more of the shortcomings set forth above, and providing further related advantages.

BRIEF SUMMARY

In one aspect, the present disclosure is directed to a system for evaluating iontophoresis devices. The system includes an impedance spectrometer, a database, and a controller. The database may take the form of stored iontophoresis device reference data. In an embodiment, the impedance spectrometer is operable to measure an impedance of an iontophoresis device and the controller is configured to perform a comparison of the measured impedance of the iontophoresis device to the stored reference data. In an embodiment, the controller is further configured to generate a response based in part on the comparison.

In another aspect, the present disclosure is directed to a method for evaluating iontophoretic delivery devices. The method includes applying at least a first test signal to an iontophoresis delivery device being evaluated, and measuring at least one resistive or capacitive response of the iontophoresis delivery device being evaluated to at least the first test signal. The method further includes comparing at least a first value, indicative of the measured at least one resistive or capacitive response of the iontophoresis delivery device, to one or more reference data sets indicative of at least one resistive or capacitive response of at least one reference iontophoresis delivery device. In an embodiment, the method further includes determining whether the iontophoresis delivery device being evaluated meets an acceptance criteria based at least in part on the comparison.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements, as drawn, are not intended to convey any information regarding the actual shape of the particular elements, and have been solely selected for ease of recognition in the drawings.

DETAILED DESCRIPTION

Figure 1:
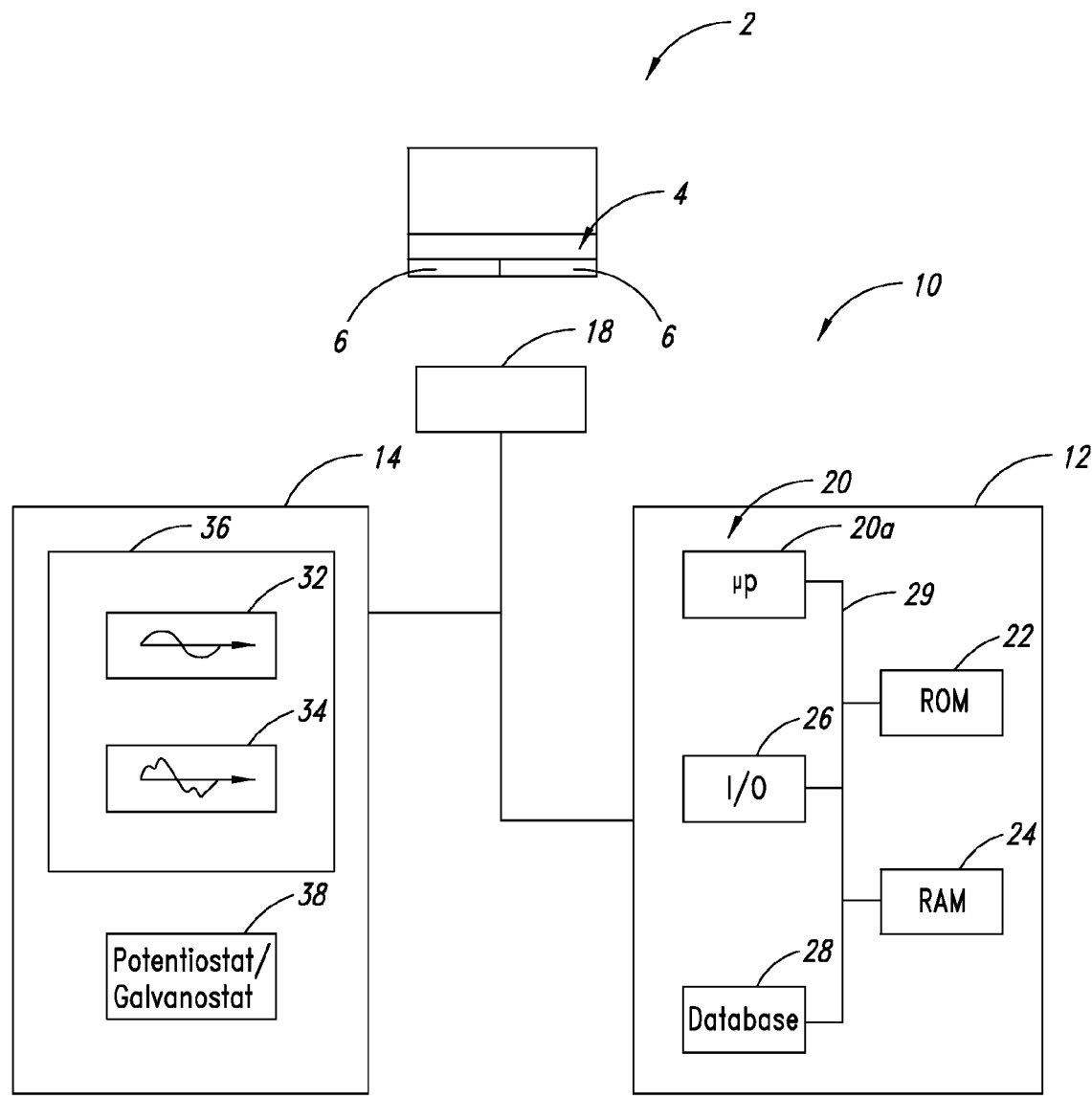
FIG. 1 is a functional block diagram showing a system for evaluating iontophoretic drug delivery devices according to one illustrative embodiment.

In the following description, certain specific details are included to provide a thorough understanding of various disclosed embodiments. One skilled in the relevant art, however, will recognize that embodiments may be practiced without one or more of these specific details, or with other methods, components, materials, etc. In other instances, well-known structures associated with impedance spectrometers, such as electrolytic sample cells, waveform generators, digital correlators, frequency response analyzers, and the like have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment," or "an embodiment," or "in another embodiment" means that a particular referent feature, structure, or characteristic described in connection with the embodiment is included in at least one embodiment. Thus, the appearance of the phrases "in one embodiment," or "in an embodiment," or "in another embodiment" in various places throughout this specification are not necessarily all referring to the same embodiment. Furthermore, the particular features, structures, or characteristics may be combined in any suitable manner in one or more embodiments.

It should be noted that, as used in this specification and the appended claims, the singular forms "a," "an," and "the" include plural referents unless the content clearly dictates otherwise. Thus, for example, reference to a system for evaluating an iontophoretic drug delivery including "a controller" includes a single controller, or two or more controllers. It should also be noted that the term "or" is generally employed in its sense including "and/or" unless the content clearly dictates otherwise.

As used herein the term "membrane" means a boundary, layer, barrier, or material, which may, or may not be permeable. The term "membrane" may further refer to an interface. Unless specified otherwise, membranes may take the form of a solid, a liquid, or a gel, and may or may not have a distinct lattice, non-cross-linked structure, or cross-linked structure.

As used herein the term "ion selective membrane" means a membrane that is substantially selective to ions, passing certain ions while blocking passage of other ions. An ion selective membrane for example, may take the form of a charge selective membrane, or may take the form of a semi-permeable membrane.

As used herein the term "charge selective membrane" means a membrane that substantially passes and/or substantially blocks ions based primarily on the polarity or charge carried by the ion. Charge selective membranes are typically referred to as ion exchange membranes, and these terms are used interchangeably herein and in the claims. Charge selective or ion exchange membranes may take the form of a cation exchange membrane, an anion exchange membrane, and/or a bipolar membrane. A cation exchange membrane substantially permits the passage of cations and substantially blocks anions. Examples of commercially available cation exchange membranes include those available under the designators NEOSEPTA, CM-1, CM-2, CMX, CMS, and CMB from Tokuyama Co., Ltd. Conversely, an anion exchange membrane substantially permits the passage of anions and substantially blocks cations. Examples of commercially available anion exchange membranes include those available under the designators NEOSEPTA, AM-1, AM-3, AMX, AHA, ACH, and ACS, also from Tokuyama Co., Ltd.

As used herein and in the claims, the term "bipolar membrane" means a membrane that is selective to two different charges or polarities. Unless specified otherwise, a bipolar membrane may take the form of a unitary membrane structure, a multiple membrane structure, or a laminate. The unitary membrane structure may include a first portion including cation ion exchange materials or groups and a second portion opposed to the first portion, including anion ion exchange materials or groups. The multiple membrane structure (e.g., two film structure) may include a cation exchange membrane laminated or otherwise coupled to an anion exchange membrane. The cation and anion exchange membranes initially start as distinct structures, and may or may not retain their distinctiveness in the structure of the resulting bipolar membrane.

As used herein and in the claims, the term "semi-permeable membrane" means a membrane that is substantially selective based on a size or molecular weight of the ion. Thus, a semi-permeable membrane substantially passes ions of a first molecular weight or size, while substantially blocking passage of ions of a second molecular weight or size, greater than the first molecular weight or size. In some embodiments, a semi-permeable membrane may permit the passage of some molecules at a first rate, and some other molecules at a second rate different from the first. In yet further embodiments, the "semi-permeable membrane" may take the form of a selectively permeable membrane allowing only certain selective molecules to pass through it.

As used herein and in the claims, the term "porous membrane" means a membrane that is not substantially selective with respect to ions at issue. For example, a porous membrane is one that is not substantially selective based on polarity, and not substantially selective based on the molecular weight or size of a subject element or compound.

As used herein and in the claims, the term "gel matrix" means a type of reservoir, which takes the form of a three dimensional network, a colloidal suspension of a liquid in a solid, a semi-solid, a cross-linked gel, a non cross-linked gel, a jelly-like state, and the like. In some embodiments, the gel matrix may result from a three dimensional network of entangled macromolecules (e.g., cylindrical micelles). In some embodiments, a gel matrix may include hydrogels, organogels, and the like. Hydrogels refer to three-dimensional network of, for example, cross-linked hydrophilic polymers in the form of a gel and substantially composed of water. Hydrogels may have a net positive or negative charge, or may be neutral.

As used herein and in the claims, the term "reservoir" means any form of mechanism to retain an element, compound, pharmaceutical composition, active agent, and the like, in a liquid state, solid state, gaseous state, mixed state and/or transitional state. For example, unless specified otherwise, a reservoir may include one or more cavities formed by a structure, and may include one or more ion exchange membranes, semi-permeable membranes, porous membranes and/or gels if such are capable of at least temporarily retaining an element or compound. Typically, a reservoir serves to retain a biologically active agent prior to the discharge of such agent by electromotive force and/or current into the biological interface. A reservoir may also retain an electrolyte solution.

As used herein and in the claims, the term "active agent" refers to a compound, molecule, or treatment that elicits a biological response from any host, animal, vertebrate, or invertebrate, including for example fish, mammals, amphibians, reptiles, birds, and humans. Examples of active agents include therapeutic agents, pharmaceutical agents, pharmaceuticals (e.g., a drug, a therapeutic compound, pharmaceutical salts, and the like) non-pharmaceuticals (e.g., a cosmetic substance, and the like), a vaccine, an immunological agent, a local or general anesthetic or painkiller, an antigen or a protein or peptide such as insulin, a chemotherapy agent, and an anti-tumor agent. In some embodiments, the term "active agent" refers to the active agent as well as to its pharmacologically active salts, pharmaceutically acceptable salts, pro-drugs, metabolites, analogs, and the like. In some further embodiment, the active agent includes at least one ionic, cationic, ionizeable and/or neutral therapeutic drug and/or pharmaceutically acceptable salts thereof. In yet other embodiments, the active agent may include one or more "cationic active agents" that are positively charged, and/or are capable of forming positive charges in aqueous media. For example, many biologically active agents have functional groups that are readily convertible to a positive ion or can dissociate into a positively charged ion and a counter ion in an aqueous medium. Other active agents may be polarized or polarizable, that is exhibiting a polarity at one portion relative to another portion. For instance, an active agent having an amino group can typically take the form an ammonium salt in solid state and dissociates into a free ammonium ion ($NH_4^+$) in an aqueous medium of appropriate pH. The term "active agent" may also refer to electrically neutral agents, molecules, or compounds capable of being delivered via electroosmotic flow. The electrically neutral agents are typically carried by the flow of, for example, a solvent during electrophoresis. Selection of the suitable active agents is therefore within the knowledge of one skilled in the relevant art.

In some embodiments, one or more active agents may be selected from analgesics, anesthetics, anesthetics vaccines, antibiotics, adjuvants, immunological adjuvants, immunogens, tolerogens, allergens, toll-like receptor agonists, toll-like receptor antagonists, immuno-adjuvants, immuno-modulators, immuno-response agents, immuno-stimulators, specific immuno-stimulators, non-specific immuno-stimulators, and immuno-suppressants, or combinations thereof.

Non-limiting examples of such active agents include lidocaine, articaine, and others of the -caine class; morphine, hydromorphone, fentanyl, oxycodone, hydrocodone, buprenorphine, methadone, and similar opioid agonists; sumatriptan succinate, zolmitriptan, naratriptan HCl, rizatriptan benzoate, almotriptan malate, frovatriptan succinate and other 5-hydroxytryptamine1 receptor subtype agonists; resiquimod, imiquidmod, and similar TLR 7 and 8 agonists and antagonists; domperidone, granisetron hydrochloride, ondansetron and such anti-emetic drugs; zolpidem tartrate and similar sleep inducing agents; L-dopa and other anti-Parkinson's medications; aripiprazole, olanzapine, quetiapine, risperidone, clozapine and ziprasidone as well as other neuroleptica; diabetes drugs such as exenatide; as well as peptides and proteins for treatment of obesity and other maladies.

Further non-limiting examples of active agents include ambucaine, amethocaine, isobutyl p-aminobenzoate, amolanone, amoxecaine, amylocaine, aptocaine, azacaine, bencaine, benoxinate, benzocaine, N,N-dimethylalanylbenzocaine, N,N-dimethylglycylbenzocaine, glycylbenzocaine, beta-adrenoceptor antagonists betoxycaine, bumecaine, bupivicaine, levobupivicaine, butacaine, butamben, butanilicaine, butethamine, butoxycaine, metabutoxycaine, carbizocaine, carticaine, centbucridine, cepacaine, cetacaine, chloroprocaine, cocaethylene, cocaine, pseudococaine, cyclomethycaine, dibucaine, dimethisoquin, dimethocaine, diperodon, dyclonine, ecognine, ecogonidine, ethyl aminobenzoate, etidocaine, euprocin, fenalcomine, fomocaine, heptacaine, hexacaine, hexocaine, hexylcaine, ketocaine, leucinocaine, levoxadrol, lignocaine, lotucaine, marcaine, mepivacaine, metacaine, methyl chloride, myrtecaine, naepaine, octacaine, orthocaine, oxethazaine, parenthoxycaine, pentacaine, phenacine, phenol, piperocaine, piridocaine, polidocanol, polycaine, prilocaine, pramoxine, procaine (Novocaine®), hydroxyprocaine, propanocaine, proparacaine, propipocaine, propoxycaine, pyrrocaine, quatacaine, rhinocaine, risocaine, rodocaine, ropivacaine, salicyl alcohol, tetracaine, hydroxytetracaine, tolycaine, trapencaine, tricaine, trimecaine tropocaine, zolamine, a pharmaceutically acceptable salt thereof, and mixtures thereof.

As used herein and in the claims, the term "subject" generally refers to any host, animal, vertebrate, or invertebrate, and includes fish, mammals, amphibians, reptiles, birds, and particularly humans.

The headings provided herein are for convenience only and do not interpret the scope or meaning of the embodiments.

FIG. 1 shows an exemplary system 10 for evaluating iontophoretic drug delivery devices. The system 10 includes a control system 12 including one or more controllers 20, such as microprocessor 20a and an impedance spectrometer 14. The system 10 may further include one or more databases 28.

The impedance spectrometer 14 is operable to measure an impedance of an iontophoresis device 2 under evaluation. Impedance is a measure of opposition to electrical current flow, and typically refers to the relationship between the voltage across a sample element and the current through the sample element. The electrical current flow results, in part, from an ionic movement response to the applied potential difference. If the applied potential (excitation or input signal) is sinusoidal (e.g., $E=E_0 \sin[\omega t]$), then the subsequent current (response or output signal) will also be sinusoidal, with a value of $I=I_0 \sin[\omega t+\phi]$. The relationship between the applied potential (E) and the current flow (I) is known as the impedance (Z). Impedance (Z) has a magnitude ($|Z|$) and phase ($\phi$) and is generally expressed as a complex vector sum of resistance (R) and reactance (X). Frequency response refers to the transfer characteristic of a system, that is, the input/output relationship. For example, the magnitude and phase shift of an alternating current (AC) response of a sample element to an applied AC.

Impedance is sometimes determined from a response to an applied test signal. The impedance spectrometer 14 may include an input signal generator 32 (e.g., a sine wave generator) configured to provide an input signal of programmable amplitude and frequency, and one or more response analyzers 34 configured to obtain magnitude and phase information from a signal response. The input signal generator 32 and one or more response analyzers 34 can be included in a single frequency response analyzer (FRA) 36, or provided as separate components. The impedance spectrometer 14 may further include a potentiostat/galvanostat 38. In an embodiment, the impedance spectrometer 14 is operable to determine the impedance for a component (e.g., an iontophoretic drug delivery patch) under evaluation, from measured values of a current and a voltage.

In some embodiments, the FRA 36 is configured to apply an excitation or test signal to an electrode assembly, an electrolytic cell, an iontophoretic delivery patch, and/or iontophoresis device that includes one or more therapeutic agents for iontophoretic drug delivery. The FRA 36 may further be configured to analyze a response signal resulting from the excitation signal. In an embodiment, the FRA 36 may be configured to provide impedance measurements in a stand-alone mode, suitable for making two, three, or four electrode impedance measurements.

The impedance spectrometer 14 may further be operable to determine the impedance of an iontophoresis device 2 for at least two selected frequencies of an alternating current. It is possible to determine various resistive and capacitive properties of an iontophoresis device 2 by varying the frequency of the applied signal. For example, in some systems the impedance of electrolytes included in the iontophoresis device 2 may be evaluated by applying one or more high frequency input signals. In some other systems, applying an input signal comprising one or more selected low frequencies may provide information regarding the capacitance at the interfaces of one or more resistive elements included in the iontophoresis device 2. Examples of a resistive element include an iontophoretic delivery patch, an iontophoresis device, a membrane (e.g., an ion selective membrane, a charge selective membrane, a bipolar membrane, a semi-permeable membrane, a porous membrane, gel-matrix, and the like), a reservoir (e.g., cavity, membrane, gel-matrix, and the like), an electrolytic cell, and the like. In an embodiment, the resistive element includes an iontophoretic drug delivery patch.

In an embodiment, the system 10 may be operable to determine the impedance of one or more electrolytes included in the iontophoresis device 2 under evaluation by applying an input signal comprising one or more selected high frequencies, and measuring the response signal. The system 10 may likewise be operable to determine the impedance of one or more interfaces included in the iontophoresis device 2 under evaluation by applying an input signal comprising one, or more selected low frequencies, and measuring the response signal. In some embodiments, the iontophoresis device 2 is evaluated before the addition of an integrated power supply.

In another embodiment, the impedance spectrometer 14 may be operable to determine the impedance of an iontophoresis device by applying a frequency-swept sine wave to the iontophoresis device 2, and examining the response signals using the one or more response analyzers 34. Determining the impedance may include, for example, determining at least one of an amplitude and phase shift of a measured signal of the iontophoresis device 2 for at least two selected frequencies of an alternating current. In an embodiment, the frequency of the alternating current is selected from a range of about 10 µHz to about 1 MHz. In another embodiment, the frequency of the alternating current is selected from three or more regions of a frequency spectrum. In yet another embodiment, the magnitude of the alternating current is selected from a range of about 10 mV to about 100 MV. In some embodiments, the iontophoresis device 2 is in the form of an iontophoretic drug delivery patch.

Evaluating the impedance of the iontophoresis device 2 may include applying a small test signal to the iontophoresis device 2 and measuring a phase delay and/or and amplitude of the response signal. In some embodiments, the magnitude of the test signal may range from about 1 mV to about 100 MV. In some other embodiments, the magnitude of the test signal is selected such that that the magnitude does not exceed the electrochemical potential of the chemical reaction associated with the electrophoresis device 2 under evaluation.

Applying a small test signal may further include applying an alternating current for a limited amount of time, or applying a limited number of cycles of an alternating current. In some embodiments, the duration of the applied small test signal is determined by the time required to apply a predetermined number of cycles. In other embodiments, applying a small test signal may include applying a test signal for a limited amount of time, typically ranging from about less than a second, to about five seconds, to the iontophoresis device 2 under evaluation.

In some embodiments, evaluating the impedance of the iontophoresis device 2 may include, for example, using two, three, or four electrodes to test the device. Selecting the proper configuration depends on many factors including whether test lead resistance contributes significantly to the measurement, the need to precisely control the potential across the electrodes, the electrolytic properties of the system under evaluation, etc. For example, a four-point electrode approach to measure impedance is useful when evaluating systems with low impedances (e.g., in the milli-ohm or µ-ohm range), measuring impedances of electrolytic systems, determining ion conductivities, evaluating processes occurring between two electrodes separated by one or more membranes, and/or determining the ion transport through one or more membranes. A typical four-point electrode configuration usually employs a pair of applying electrodes and a pair of sensing electrodes. The applying electrodes enable a current flow, and the sensing electrodes (whose characteristics are well known over the range of the applied signal) measure a voltage drop across the component (e.g., an iontophoretic drug delivery patch) under evaluation. In some embodiments, the electrodes should be selected from the same or similar materials employed in the iontophoresis device's electrode assembly to minimize generating a potential due in part to the differences in the standard potentials associated with the various materials. Suitable materials may include, for example, silver (Ag) and silver chloride (AgCl).

The system 10 may further include a test interface 18 communicatively coupled to the impedance spectrometer 14 and selectively positionable with respect to an iontophoresis device 2 being evaluated, such that the test interface 18 is able to make electrical contact with at least a portion 4 of the iontophoresis device 2 being evaluated. In some embodiment, the portion 4 of the iontophoresis device 2 includes at least two distinct electrical contacts 6. In another embodiment, the test interface 18 includes four electrodes and is operable to perform a four-point impedance measurement.

In some embodiments, a portion 4 of the iontophoresis device 2 may include an interface electrically coupleable to at least two electrodes that are operable for measuring the impedance of the iontophoresis device 2. The portion 4 of the iontophoresis device 2 may take the form an electrical contact surface. In other embodiments, the portion 4 of the iontophoresis device may take the form of a surface operable to provide two or more electrical contacts 6 for measuring the impedance of the iontophoresis device using, for example, a four-point electrode configuration.

The control system 12 may include one or more controllers 20 such as the microprocessor 20a, a digital signal processor (DSP) (not shown), an application-specific integrated circuit (ASIC) (not shown), and the like. The control system 12 may also include one or more memories, for example, read-only memory (ROM) 22 random access memory (RAM) 24, and the like, coupled to the controllers 20 by one or more busses 29. The control system 12 may further include one or more input devices 26 (e.g., a display, a mouse, a keyboard, and other peripheral devices). In an embodiment, the microprocessor 20 may be configured to compare the determined impedance of the iontophoresis device 2 under evaluation to a database 28 of stored values.

The database 28 of stored values may include impedance data, flux data, ionic conductivity data, resistance data, reactance data, ionic mobility data, diffusion coefficients, transport numbers, statistical averages data for general iontophoretic trends, and the like. The database 28 of stored values may further include electrolyte specific impedance data, membrane specific impedance data, resistive element specific impedance data, iontophoresis device specific impedance data, interface specific impedance data, and the like.

In an embodiment, the controller 20 may further be configured to perform a comparison of the measured impedance of the iontophoresis device 2 to the stored reference data. In an embodiment, the stored reference data includes impedance data, characteristic phase delay data, characteristic amplitude data, characteristic resistance data, characteristic electrolyte resistance data, characteristic interface capacitance data, characteristic ionic movement data, and the like. In an embodiment, the characteristic phase delay data comprises phase delay data at two or more frequencies of an alternating current, and the characteristic amplitude data comprises amplitude data at two or more frequencies of the alternating current. In another embodiment, the characteristic phase delay data comprises one or more phase delay ranges; and the characteristic amplitude data comprises one or more amplitude ranges. In other embodiments, the characteristic phase delay data comprises "fingerprint" characteristics of a compliant and/or reference iontophoresis device. The fingerprint characteristics may include phase shifts and amplitudes measured at various frequencies reflective of the components of the iontophoretic system or device under evaluation.

The controller 20 may further be configured to perform a comparison of the measured impedance of the iontophoresis device to the stored reference data, and to generate a response based in part on the comparison. The response may include at least one of a comparison plot, a compliance code, a diagnostic code, a test code, an alarm, and a rating value. The response may further include a measure of deviation between the measured impedance of the iontophoresis device and the corresponding stored reference data.

Figure 2:
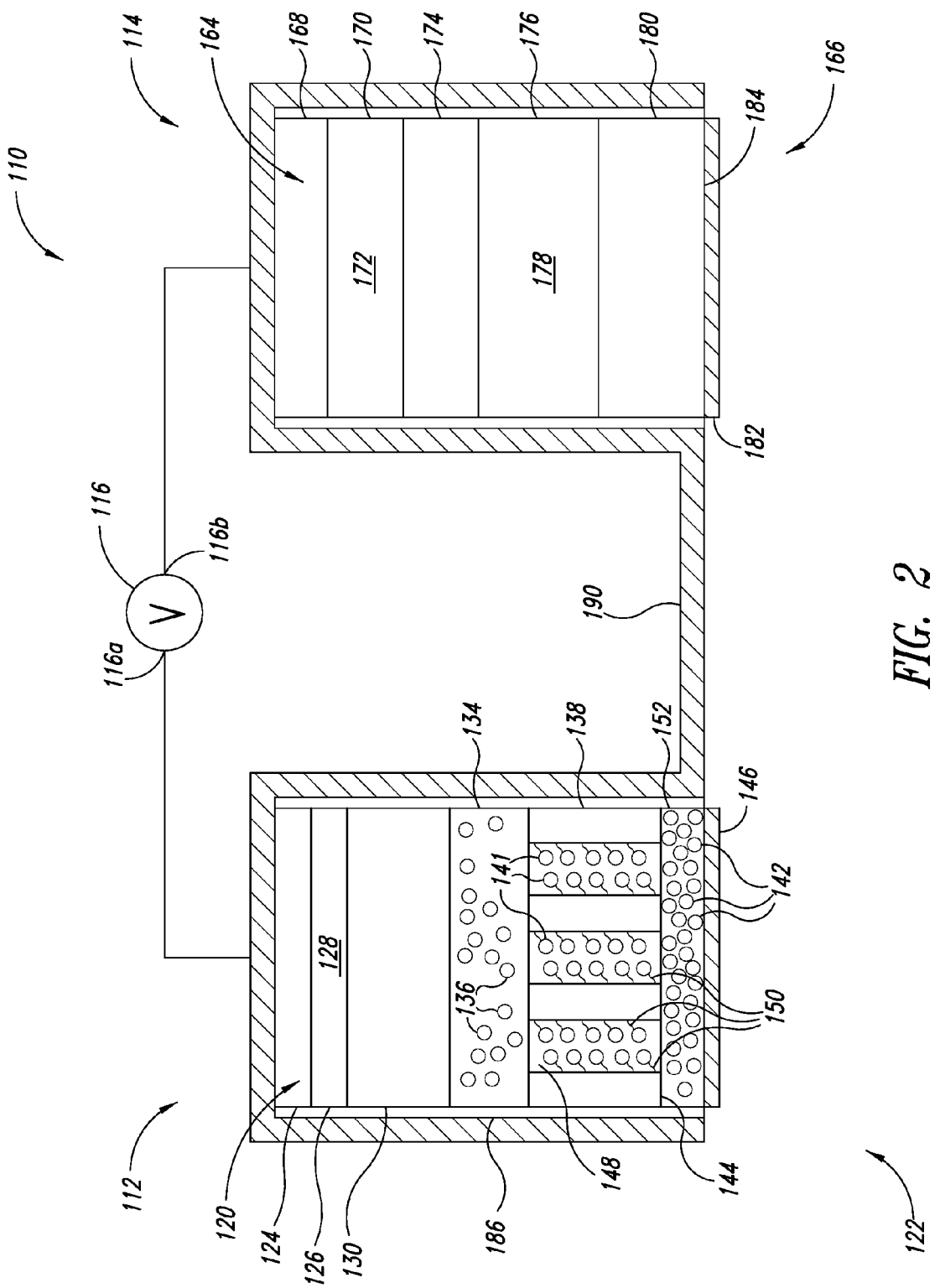
FIG. 2 is a schematic diagram of an iontophoresis device including active and counter electrode assemblies, and a power source according to another illustrated embodiment.
Figure 3:
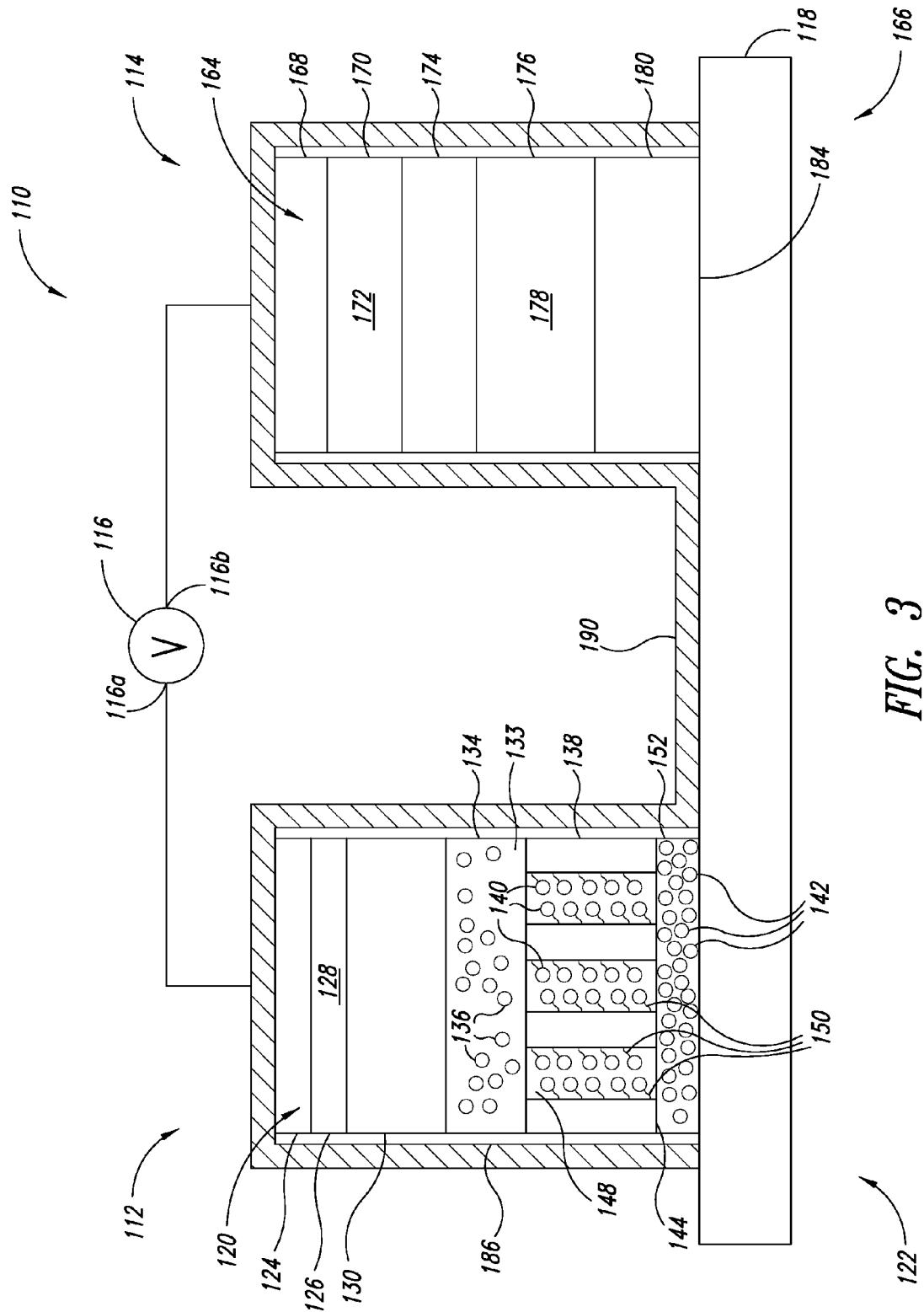
FIG. 3 is a schematic diagram of the iontophoresis device of FIG. 2 positioned on a biological interface, with the outer release liner removed to expose the active agent according to another illustrated embodiment.

FIGS. 2 and 3 show an exemplary iontophoresis device 100 comprising active and counter electrode assemblies 112, 114, respectively, electrically coupleable to an integrated power source 116 to supply an active agent contained in the active electrode assembly 112 to a biological interface 118 (FIG. 2), such as a portion of skin or mucous membrane via iontophoresis. Typically, the iontophoresis device 100 is evaluated before the addition of the integrated power source 116.

In the illustrated embodiment, the active electrode assembly 112 comprises, from an interior 120 to an exterior 122 of the active electrode assembly 112: an active electrode element 124, an electrolyte reservoir 126 storing an electrolyte 128, an inner ion selective membrane 130, an inner active agent reservoir 134, storing active agent 136, an optional outermost ion selective membrane 138 that optionally caches additional active agent 140, an optional further active agent 142 carried by an outer surface 144 of the outermost ion selective membrane 138, and an optional outer release liner 146. The active electrode assembly 112 may further comprise an optional inner sealing liner (not shown) between two layers of the active electrode assembly 112, for example, between the inner ion selective membrane 130 and the inner active agent reservoir 134. The inner sealing liner, if present, would be removed prior to application of the iontophoretic device to the biological surface 118. Each of the above elements or structures will be discussed in detail below.

The active electrode element 124 is electrically coupled to a first pole 116a of the power source 116 and positioned in the active electrode assembly 112 to apply an electromotive force to transport the active agent 136, 140, 142 via various other components of the active electrode assembly 112. Under ordinary use conditions, the magnitude of the applied electromotive force is generally that required to deliver the one or more active agents according to a therapeutic effective dosage protocol. In some embodiments, the magnitude is selected such that it meets or exceeds the ordinary use operating electrochemical potential of the iontophoresis delivery device 100. In some other embodiments, the magnitude of the applied electromotive force under normal conditions, generally exceeds the magnitude of the applied electromotive force supplied to the iontophoresis delivery device 100 when it is undergoing evaluation.

The active electrode element 124 may take a variety of forms. In one embodiment, the device may advantageously employ a carbon-based active electrode element 124. Such may, for example, comprise multiple layers, for example a polymer matrix comprising carbon and a conductive sheet comprising carbon fiber or carbon fiber paper, such as that described in commonly assigned pending Japanese patent application 2004/317317, filed Oct. 29, 2004. The carbon-based electrodes are inert electrodes in that they do not themselves undergo or participate in electrochemical reactions. Thus, an inert electrode distributes current through the oxidation or reduction of a chemical species capable of accepting or donating an electron at the potential applied to the system, (e.g., generating ions by either reduction or oxidation of water). Additional examples of inert electrodes include stainless steel, gold, platinum, capacitive carbon, or graphite.

Alternatively, an active electrode of sacrificial conductive material, such as a chemical compound or amalgam, may also be used. A sacrificial electrode does not cause electrolysis of water, but would itself be oxidized or reduced. Typically, for an anode a metal/metal salt may be employed. In such case, the metal would oxidize to metal ions, which would then be precipitated as an insoluble salt. An example of such anode includes an Ag/AgCl electrode. The reverse reaction takes place at the cathode in which the metal ion is reduced and the corresponding anion is released from the surface of the electrode.

The electrolyte reservoir 126 may take a variety of forms including any structure capable of retaining electrolyte 128, and in some embodiments may even be the electrolyte 128 itself, for example, where the electrolyte 128 is in a gel, semi-solid or solid form. For example, the electrolyte reservoir 126 may take the form of a pouch or other receptacle, or a membrane with pores, cavities, or interstices, particularly where the electrolyte 128 is a liquid.

In one embodiment, the electrolyte 128 comprises ionic or ionizable components in an aqueous medium, which can act to conduct current towards or away from the active electrode element. Suitable electrolytes include, for example, aqueous solutions of salts. Preferably, the electrolyte 128 includes salts of physiological ions, such as, sodium, potassium, chloride, and phosphate.

Once an electrical potential is applied, when an inert electrode element is in use, water is electrolyzed at both the active and counter electrode assemblies. In certain embodiments, such as when the active electrode assembly is an anode, water is oxidized. As a result, oxygen is removed from water while protons ($H^+$) are produced. In one embodiment, the electrolyte 128 may further comprise an anti-oxidant. In some embodiments, the anti-oxidant is selected from anti-oxidants that have a lower potential than that of, for example, water. In such embodiments, the selected anti-oxidant is consumed rather than having the hydrolysis of water occur. In some further embodiments, an oxidized form of the anti-oxidant is used at the cathode and a reduced form of the anti-oxidant is used at the anode. Examples of biologically compatible anti-oxidants include, but are not limited to ascorbic acid (vitamin C), tocopherol (vitamin E), or sodium citrate.

As noted above, the electrolyte 128 may be in the form of an aqueous solution housed within a reservoir 126, or may take the form of a dispersion in a hydrogel, organogel, or hydrophilic polymer capable of retaining a substantial amount of water or solvent. For instance, a suitable electrolyte may take the form of a solution of 0.5 M disodium fumarate: 0.5 M polyacrylic acid: 0.15 M anti-oxidant.

The inner ion selective membrane 130 is generally positioned to separate the electrolyte 128 and the inner active agent reservoir 134, if such a membrane is included within the device. The inner ion selective membrane 130 may take the form of a charge selective membrane. For example, when the active agent 136, 140, 142 comprises a cationic active agent, the inner ion selective membrane 130 may take the form of an anion exchange membrane, selective to substantially pass anions and substantially block cations. The inner ion selective membrane 130 may advantageously prevent transfer of undesirable elements or compounds between the electrolyte 128 and the inner active agent reservoir 34. For example, the inner ion selective membrane 130 may prevent or inhibit the transfer of sodium (Na$^+$) ions from the electrolyte 128, thereby increasing the transfer rate and/or biological compatibility of the iontophoresis device 110.

The inner active agent reservoir 134 is generally positioned between the inner ion selective membrane 130 and the outermost ion selective membrane 138. The inner active agent reservoir 134 may take a variety of forms including any structure capable of temporarily retaining active agent 136. For example, the inner active agent reservoir 134 may take the form of a pouch or other receptacle, a membrane with pores, cavities, or interstices, particularly where the active agent 136 is a liquid. The inner active agent reservoir 134 further may comprise a gel matrix.

Optionally, an outermost ion selective membrane 138 is positioned generally opposed across the active electrode assembly 112 from the active electrode element 124. The outermost membrane 138 may, as in the embodiment illustrated in FIGS. 2 and 3, take the form of an ion exchange membrane having pores 148 (only one called out in FIGS. 2 and 3 for sake of clarity of illustration) of the ion selective membrane 138 including ion exchange material or groups 150 (only three called out in FIGS. 2 and 3 for sake of clarity of illustration). Under the influence of an electromotive force or current, the ion exchange material or groups 150 selectively substantially passes ions of the same polarity as active agent 136, 140, while substantially blocking ions of the opposite polarity. Thus, the outermost ion exchange membrane 138 is charge selective. Where the active agent 136, 140, 142 is a cation (e.g., lidocaine), the outermost ion selective membrane 138 may take the form of a cation exchange membrane, thus allowing the passage of the cationic active agent while blocking the back flux of the anions present in the biological interface, such as skin.

The outermost ion selective membrane 138 may optionally cache active agent 140. Without being limited by theory, the ion exchange groups or material 150 temporarily retains ions of the same polarity as the polarity of the active agent in the absence of electromotive force or current and substantially releases those ions when replaced with substitutive ions of like polarity or charge under the influence of an electromotive force or current.

Alternatively, the outermost ion selective membrane 138 may take the form of semi-permeable or microporous membrane that is selective by size. In some embodiments, such a semi-permeable membrane may advantageously cache active agent 140, for example by employing the removably releasable outer release liner 146 to retain the active agent 140 until the outer release liner 146 is removed prior to use.

The outermost ion selective membrane 138 may be optionally preloaded with the additional active agent 140, such as ionized or ionizable drugs or therapeutic agents and/or polarized or polarizable drugs or therapeutic agents. Where the outermost ion selective membrane 138 is an ion exchange membrane, a substantial amount of active agent 140 may bond to ion exchange groups 150 in the pores, cavities or interstices 148 of the outermost ion selective membrane 138.

The active agent 142 that fails to bond to the ion exchange groups of material 150 may adhere to the outer surface 144 of the outermost ion selective membrane 138 as the further active agent 142. Alternatively, or additionally, the further active agent 142 may be positively deposited on and/or adhered to at least a portion of the outer surface 144 of the outermost ion selective membrane 138, for example, by spraying, flooding, coating, electrostatically depositing, vapor depositioning, and/or otherwise. In some embodiments, the further active agent 142 may sufficiently cover the outer surface 144 and/or be of sufficient thickness to form a distinct layer 152. In other embodiments, the further active agent 142 may not be sufficient in volume, thickness, or coverage as to constitute a layer in a conventional sense of such term.

The active agent 142 may be deposited in a variety of highly concentrated forms such as, for example, solid form, nearly saturated solution form or gel form. If in solid form, a source of hydration may be provided, either integrated into the active electrode assembly 112, or applied from the exterior thereof just prior to use.

In some embodiments, the active agent 136, additional active agent 140, and/or further active agent 142 may be identical or similar compositions or elements. In other embodiments, the active agent 136, additional active agent 140, and/or further active agent 142 may be different compositions or elements from one another. Thus, a first type of active agent may be stored in the inner active agent reservoir 134, while a second type of active agent may be cached in the outermost ion selective membrane 138. In such an embodiment, either the first type or the second type of active agent may be deposited on the outer surface 144 of the outermost ion selective membrane 138 as the further active agent 142. Alternatively, a mix of the first and the second types of active agent may be deposited on the outer surface 144 of the outermost ion selective membrane 138 as the further active agent 142. As a further alternative, a third type of active agent composition or element may be deposited on the outer surface 144 of the outermost ion selective membrane 138 as the further active agent 142. In another embodiment, a first type of active agent may be stored in the inner active agent reservoir 134 as the active agent 136 and cached in the outermost ion selective membrane 138 as the additional active agent 140, while a second type of active agent may be deposited on the outer surface 144 of the outermost ion selective membrane 138 as the further active agent 142. Typically, in embodiments where one or more different active agents are employed, the active agents 136, 140, 142 will all be of common polarity to prevent the active agents 136, 140, 142 from competing with one another. Other combinations are possible.

The outer release liner 146 may generally be positioned overlying or covering further active agent 142 carried by the outer surface 144 of the outermost ion selective membrane 138. The outer release liner 146 may protect the further active agent 142 and/or outermost ion selective membrane 138 during storage, prior to application of an electromotive force or current. The outer release liner 146 may be a selectively releasable liner made of waterproof material, such as release liners commonly associated with pressure sensitive adhesives. Note that the outer release liner 146 is shown in place in FIG. 2 and removed in FIG. 3.

An interface-coupling medium (not shown) may be employed between the electrode assembly and the biological interface 118. The interface coupling medium may take the form of, for example, an adhesive and/or gel. The gel may take the form of, for example, a hydrating gel. Selection of suitable bioadhesive gels is within the knowledge of one skilled in the relevant art.

In the embodiment illustrated in FIGS. 2 and 3, the counter electrode assembly 114 comprises, from an interior 164 to an exterior 166 of the counter electrode assembly 114: a counter electrode element 168, an electrolyte reservoir 170 storing an electrolyte 172, an inner ion selective membrane 174, an optional buffer reservoir 176 storing buffer material 178, an optional outermost ion selective membrane 180, and an optional outer release liner 182.

The counter electrode element 168 is electrically coupleable via a second pole 116b to the power source 116, the second pole 116b having an opposite polarity to the first pole 116a. In one embodiment, the counter electrode element 168 is an inert electrode. For example, the counter electrode element 168 may be the carbon-based electrode element discussed above.

The electrolyte reservoir 170 may take a variety of forms including any structure capable of retaining electrolyte 172, and in some embodiments may even be the electrolyte 172 itself, for example, where the electrolyte 172 is in a gel, semi-solid or solid form. For example, the electrolyte reservoir 170 may take the form of a pouch or other receptacle, or a membrane with pores, cavities or interstices, particularly where the electrolyte 172 is a liquid.

The electrolyte 172 is generally positioned between the counter electrode element 168 and the outermost ion selective membrane 180, proximate the counter electrode element 168. As described above, the electrolyte 172 may provide ions or donate charges to prevent or inhibit the formation of gas bubbles (e.g., hydrogen or oxygen, depending on the polarity of the electrode) on the counter electrode element 168 and may prevent or inhibit the formation of acids or bases or neutralize the same, which may enhance efficiency and/or reduce the potential for irritation of the biological interface 118.

The inner ion selective membrane 174 may be positioned between the electrolyte 172 and the buffer material 178. The inner ion selective membrane 174 may take the form of a charge selective membrane, such as the illustrated ion exchange membrane that substantially allows passage of ions of a first polarity or charge while substantially blocking passage of ions or charge of a second, opposite polarity. The inner ion selective membrane 174 will typically pass ions of opposite polarity or charge to those passed by the outermost ion selective membrane 180 while substantially blocking ions of like polarity or charge. Alternatively, the inner ion selective membrane 174 may take the form of a semi-permeable or microporous membrane that is selective based on size.

The inner ion selective membrane 174 may prevent transfer of undesirable elements or compounds into the buffer material 178. For example, the inner ion selective membrane 174 may prevent or inhibit the transfer of hydroxy ($OH^-$) or chloride ($Cl^-$) ions from the electrolyte 172 into the buffer material 178.

The optional buffer reservoir 176 is generally disposed between the electrolyte reservoir and the outermost ion selective membrane 180. The buffer reservoir 176 may take a variety of forms capable of temporarily retaining the buffer material 178. For example, the buffer reservoir 176 may take the form of a cavity, a porous membrane or a gel.

The buffer material 178 may supply ions for transfer through the outermost ion selective membrane 142 to the biological interface 118. Consequently, the buffer material 178 may comprise, for example, a salt (e.g., NaCl).

The outermost ion selective membrane 180 of the counter electrode assembly 114 may take a variety of forms. For example, the outermost ion selective membrane 180 may take the form of a charge selective ion exchange membrane. Typically, the outermost ion selective membrane 180 of the counter electrode assembly 114 is selective to ions with a charge or polarity opposite to that of the outermost ion selective membrane 138 of the active electrode assembly 112. The outermost ion selective membrane 180 is therefore an anion exchange membrane, which substantially passes anions and blocks cations, thereby prevents the back flux of the cations from the biological interface. Examples of suitable ion exchange membranes include, but are not limited to, the examples discussed above.

Alternatively, the outermost ion selective membrane 180 may take the form of a semi-permeable membrane that substantially passes and/or blocks ions based on size or molecular weight of the ion.

The outer release liner 182 may generally be positioned overlying or covering an outer surface 184 of the outermost ion selective membrane 180. Note that the outer release liner 182 is shown in place in FIG. 2 and removed in FIG. 3. The outer release liner 182 may protect the outermost ion selective membrane 180 during storage, prior to application of an electromotive force or current. The outer release liner 182 may be a selectively releasable liner made of waterproof material, such as release liners commonly associated with pressure sensitive adhesives. In some embodiments, the outer release liner 182 may be coextensive with the outer release liner 146 of the active electrode assembly 112.

The iontophoresis device 110 may further comprise an inert molding material 186 adjacent exposed sides of the various other structures forming the active and counter electrode assemblies 112, 114. The molding material 186 may advantageously provide environmental protection to the various structures of the active and counter electrode assemblies 112, 114. Enveloping the active and counter electrode assemblies 112, 114 is a housing material 190.

As best seen in FIG. 3, the active and counter electrode assemblies 112, 114 are positioned on the biological interface 118. Positioning on the biological interface may close the circuit, allowing electromotive force to be applied and/or current to flow from one pole 116a of the power source 116 to the other pole 116b, via the active electrode assembly, biological interface 118 and counter electrode assembly 114.

In use, the outermost active electrode ion selective membrane 138 may be placed directly in contact with the biological interface 118. Alternatively, an interface-coupling medium (not shown) may be employed between the outermost active electrode ion selective membrane 122 and the biological interface 118. The interface-coupling medium may take the form of, for example, an adhesive and/or gel. The gel may take the form of, for example, a hydrating gel or a hydrogel. If used, the interface-coupling medium should be permeable by the active agent 136, 140, 142.

In some embodiments, the power source 116 is selected to provide sufficient voltage, current, and/or duration to ensure delivery of the one or more active agents 136, 140, 142 from the reservoir 134 and across a biological interface (e.g., a membrane) to impart the desired physiological effect. The power source 116 may take the form of one or more chemical battery cells, super- or ultra-capacitors, or fuel cells. The power source 116 may, for example, provide a voltage of 12.8 V DC, with tolerance of 0.8 V DC, and a current of 0.3 mA. The power source 116 may be selectively electrically coupled to the active and counter electrode assemblies 112, 114 via a control circuit, for example, via carbon fiber ribbons. The iontophoresis device 10 may include discrete and/or integrated circuit elements to control the voltage, current and/or power delivered to the electrode assemblies 112, 114. For example, the iontophoresis device 110 may include a diode to provide a constant current to the electrode elements 124, 168.

As suggested above, the active agent 136, 140, 142 may take the form of cationic, anionic, ionizeable, and/or neutral drugs or other therapeutic agent. Consequently, the poles or terminals of the power source 116 and the selectivity of the outermost ion selective membranes 138, 180 and inner ion selective membranes 130, 174 are selected accordingly.

During iontophoresis, the electromotive force across the electrode assemblies, as described, leads to a migration of charged active agent molecules, as well as ions and other charged components, through the biological interface into the biological tissue. This migration may lead to an accumulation of active agents, ions, and/or other charged components within the biological tissue beyond the interface. During iontophoresis, in addition to the migration of charged molecules in response to repulsive forces, there is also an electroosmotic flow of solvent (e.g., water) through the electrodes and the biological interface into the tissue. In certain embodiments, the electroosmotic solvent flow enhances migration of both charged and uncharged molecules. Enhanced migration via electroosmotic solvent flow may occur particularly with increasing size of the molecule.

In certain embodiments, the active agent may be a higher molecular weight molecule. In certain aspects, the molecule may be a polar polyelectrolyte. In certain other aspects, the molecule may be lipophilic. In certain embodiments, such molecules may be charged, may have a low net charge, or may be uncharged under the conditions within the active electrode. In certain aspects, such active agents may migrate poorly under the iontophoretic repulsive forces, in contrast to the migration of small more highly charged active agents under the influence of these forces. These higher molecular weight active agents may thus be carried through the biological interface into the underlying tissues primarily via electroosmotic solvent flow. In certain embodiments, the high molecular weight polyelectrolytic active agents may be proteins, polypeptides or nucleic acids. In other embodiments, the active agent may be mixed with another agent to form a complex capable of being transported across the biological interface via one of the motive methods described above.

Figure 4:
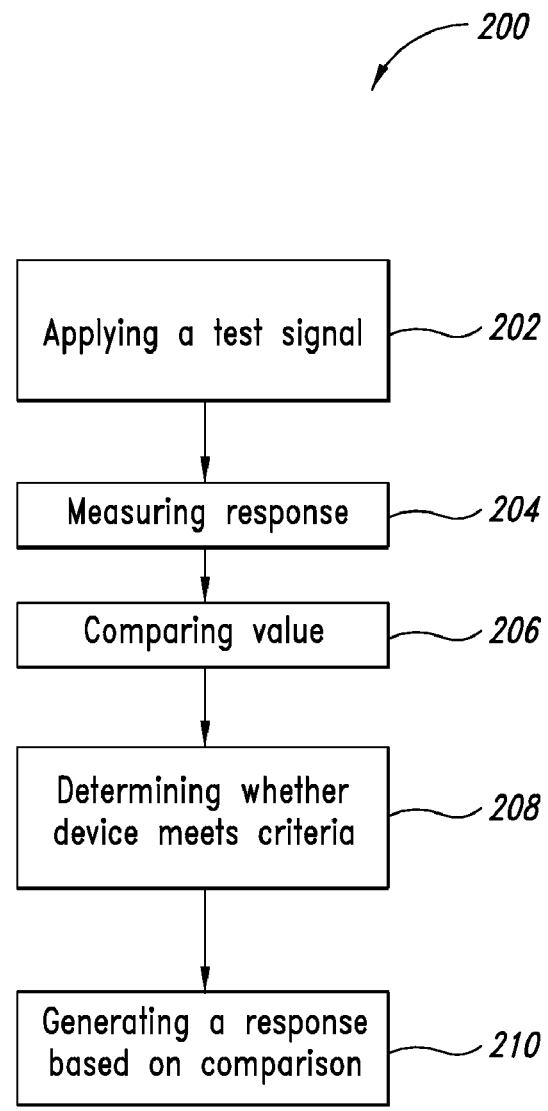
FIG. 4 is a flow diagram of a method for evaluating iontophoretic delivery devices according to another illustrative embodiment.

FIG. 4 shows a method 200 for evaluating iontophoretic delivery devices according to one illustrative embodiment.

At 202, the method includes applying at least a first test signal to an iontophoresis delivery device 2 being evaluated. In some embodiments, applying at least a first test signal to an iontophoresis delivery device 2 being evaluated includes applying an alternating current to the iontophoretic delivery device 2. For example, the FPA 36 is configured to apply an alternating current to an iontophoresis delivery device 2 undergoing evaluation. The applied alternating current may include an input signal of programmable amplitude and frequency, a frequency-swept sine wave, a generated waveform, a single sine wave, a multi-sine wave, and the like. In some embodiments, the alternating current is applied to an iontophoretic delivery patch, an iontophoretic drug delivery device, an electrolytic sample cell, and the like.

Applying at least a first test signal to an iontophoresis delivery device 2 being evaluated, may include applying at least a first test signal via a pair of applying electrodes included in a four-point electrode assembly. The applying electrodes enable a current flow across the component (e.g., an iontophoretic drug delivery patch) under evaluation. In some embodiments, the iontophoresis delivery device 2 is being evaluated prior to receiving a discrete power source 116 (FIGS. 2 and 3).

The magnitude of the at least a first test signal may be selected such that it does not exceed an electrochemical potential of the iontophoresis delivery device 2 being evaluated. In some embodiments, the magnitude of the at least a first test signal ranges from about 10 mV to about 100 MV. In some embodiments, applying at least a first test signal to an iontophoresis delivery device 2 being evaluated may include applying a first alternating current of a first frequency to the iontophoretic delivery device 2 being evaluated at a first time, and applying a second alternating current of a second frequency to the iontophoretic delivery device 2 being evaluated at a second time, the second frequency different than the first frequency.

At 204, the method 200 includes measuring at least one resistive or capacitive response of the iontophoresis delivery device 2 being evaluated to at least the first test signal. In some embodiments, measuring at least one resistive or capacitive response of the iontophoresis delivery device 2 being evaluated includes measuring at least one of a magnitude or a phase shift of a response signal with an impedance spectrometer. For example, the one or more response analyzers 34 may be configured to analyze the impedance response of an iontophoresis delivery device 2 undergoing evaluation to at least the first test signal. In some embodiments, measuring at least one resistive or capacitive response may include employing one or more data acquisition techniques including alternating current bridges (e.g., for measuring ac resistance, capacitance, and inductance), fast fourier transform techniques, lissajous figures, and phase sensitive detectors (e.g., lock-in amplifiers), sine correlation, and the like. Measuring the impedance response may further include measuring the impedance response at two or more frequencies of the alternating current, and obtaining at least one of an amplitude or a phase shift for each response signal. In certain embodiments, measuring at least one resistive or capacitive response may further include measuring the impedance response of a component of the iontophoresis delivery device 2 through at least one resistive element. Examples of a resistive element include an iontophoretic delivery patch, a membrane (e.g., an ion selective membrane, a charge selective membrane, a bipolar membrane, a semi-permeable membrane, a porous membrane, gel-matrix, and the like), and interface, a reservoir, an electrolytic cell, and the like. In an embodiment, the resistive element includes an iontophoretic drug delivery patch operable to deliver the at least one active agent. In some embodiments, measuring at least one resistive or capacitive response may include, for example, employing a pair of sensing electrodes from a typical four-point electrode configuration to measure a voltage drop across the component (e.g., an iontophoretic drug delivery patch) under evaluation.

In some embodiments, measuring at least one resistive or capacitive response of the iontophoresis delivery device 2 being evaluated includes measuring at least one of a magnitude or a phase shift of a response signal to each of a first and a second alternating currents with an impedance spectrometer.

At 206, the method 200 includes comparing at least a first value indicative of the measured at least one resistive or capacitive response of the iontophoresis delivery device 2 to one or more reference data sets indicative of at least one resistive or capacitive response of at least one reference iontophoresis delivery device. The one or more reference data sets may include may include, for example, impedance data, flux data, ionic conductivity data, resistance data, reactance data, ionic mobility data, diffusion coefficients, transport numbers, statistical averages data for general iontophoretic trends, electrolyte specific impedance data, membrane specific impedance data, resistive element specific impedance data, iontophoresis device specific impedance data, interface specific impedance data, and the like. In some embodiments, the one or more reference data sets may include "fingerprint" characteristic data of a compliant and/or reference iontophoresis device. The fingerprint characteristics may include phase shifts and amplitudes measured at various frequencies that are reflective of the components of the iontophoretic system or device 2 under evaluation. In some embodiments, the one or more controllers 20 such as a microprocessor 20a may be configured to compare the at least a first value indicative of the measured at least one resistive or capacitive response of the iontophoresis delivery device 2 to the one or more reference data sets. In some embodiments, the one or more reference data sets comprise one or more magnitude ranges or phase shift ranges of a measured response from a plurality of reference iontophoretic delivery devices to alternating current at two or more frequencies.

At 208, the method 200 includes determining whether the iontophoresis delivery device 2 undergoing evaluation meets one or more acceptance criteria based at least in part on the comparison. In an embodiment, determining whether the iontophoresis delivery device 2 being evaluated meets one or more acceptance criteria may include determining a measure of deviation between the measured impedance of the iontophoresis delivery device 2 and the corresponding one or more acceptance criteria indicative of a compliant iontophoresis delivery device 2. In some embodiments, the one or more controllers 20 such as a microprocessor 20a may be configured to compare a measured resistive or capacitive property of an iontophoretic delivery device 2 undergoing evaluation, to values stored in the one or more reference data sets.

At 210, the method 200 may further include generating a response based in part on the comparison. The generated response may include at least one of a comparison plot, a compliance code, a diagnostic code, a test code, an alarm, and a rating value. In some embodiments, the one or more controllers 20 such as a microprocessor 20a may be configured to generate the response based in part on the comparison.

The above description of illustrated embodiments, including what is described in the Abstract, is not intended to be exhaustive or to limit the embodiments to the precise forms disclosed. Although specific embodiments and examples are described herein for illustrative purposes, various equivalent modifications can be made without departing from the spirit and scope of the disclosure, as will be recognized by those skilled in the relevant art. The teachings provided herein of the various embodiments can be applied to other problem-solving systems devices, and methods, not necessarily the exemplary problem-solving systems devices, and methods generally described above.

For instance, the foregoing detailed description has set forth various embodiments of the systems, devices, and/or methods via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

In addition, those skilled in the art will appreciate that the mechanisms of taught herein are capable of being distributed as a program product in a variety of forms, and that an illustrative embodiment applies equally regardless of the particular type of signal bearing media used to actually carry out the distribution. Examples of signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety, including but not limited to:

U.S. Provisional Patent Application No. 60/842,445, filed Sep. 5, 2006; Japanese patent application Serial No. H03-86002, filed Mar. 27, 1991, having Japanese Publication No. H04-297277, issued on Mar. 3, 2000 as Japanese Patent No. 3040517; Japanese patent application Serial No. 11-033076, filed Feb. 10, 1999, having Japanese Publication No. 2000-229128; Japanese patent application Serial No. 11-033765, filed Feb. 12, 1999, having Japanese Publication No. 2000-229129; Japanese patent application Serial No. 11-041415, filed Feb. 19, 1999, having Japanese Publication No. 2000-237326; Japanese patent application Serial No. 11-041416, filed Feb. 19, 1999, having Japanese Publication No. 2000-237327; Japanese patent application Serial No. 11-042752, filed Feb. 22, 1999, having Japanese Publication No. 2000-237328; Japanese patent application Serial No. 11-042753, filed Feb. 22, 1999, having Japanese Publication No. 2000-237329; Japanese patent application Serial No. 11-099008, filed Apr. 6, 1999, having Japanese Publication No. 2000-288098; Japanese patent application Serial No. 11-099009, filed Apr. 6, 1999, having Japanese Publication No. 2000-288097; PCT patent application WO 2002JP4696, filed May 15, 2002, having PCT Publication No WO03037425; U.S. patent application Ser. No. 10/488,970, filed Mar. 9, 2004; Japanese patent application 2004/317317, filed Oct. 29, 2004; U.S. provisional patent application Ser. No. 60/627,952, filed Nov. 16, 2004; Japanese patent application Serial No. 2004-347814, filed Nov. 30, 2004; Japanese patent application Serial No. 2004-357313, filed Dec. 9, 2004; Japanese patent application Serial No. 2005-027748, filed Feb. 3, 2005; and Japanese patent application Serial No. 2005-081220, filed Mar. 22, 2005.

Aspects of the embodiments can be modified, if necessary, to employ systems, circuits, and concepts of the various patents, applications, and publications to provide yet further embodiments.

These and other changes can be made to the embodiments in light of the above-detailed description. In general, in the following claims, the terms used should not be construed to limit the invention to the specific embodiments disclosed in the specification and the claims, but should be construed to include all possible embodiments along with the full scope of equivalents to which such claims are entitled. Accordingly, the scope of the invention shall only be construed and defined by the scope of the appended claims.

What is claimed is:

1. A method for evaluating iontophoretic delivery devices, the method comprising:
applying at least a first test signal to an iontophoresis delivery device being evaluated;
measuring at least one resistive or capacitive response of the iontophoresis delivery device being evaluated to at least the first test signal;
comparing at least a first value indicative of the measured at least one resistive or capacitive response of the iontophoresis delivery device to one or more reference data sets indicative of at least one resistive or capacitive response of at least one reference iontophoresis delivery device; and
determining whether the iontophoresis delivery device being evaluated meets an acceptance criteria based at least in part on the comparison, wherein applying at least a first test signal to an iontophoresis delivery device being evaluated includes applying an alternating current to the iontophoretic delivery device.

2. The method of claim 1 wherein measuring at least one resistive or capacitive response of the iontophoresis delivery device being evaluated includes measuring at least one of a magnitude or a phase shift of a response signal with an impedance spectrometer.

3. The method of claim 1 wherein the one or more reference data sets comprise one or more magnitude ranges or phase shift ranges of a measured response from a plurality of reference iontophoretic delivery devices to alternating current at two or more frequencies.

4. The method of claim 1 wherein the applying of at least the first test signal occurs while the iontophoresis delivery device does not have a discrete power source.

5. The method of claim 1 wherein the magnitude of the at least a first test signal does not exceed an electrochemical potential of the iontophoresis delivery device being evaluated.

6. The method of claim 1 wherein the magnitude of the at least a first test signal ranges from about 10 mV to about 100 MV.

7. The method of claim 1, further comprising:
generating a response based in part on the comparison, wherein the response comprises at least one of a comparison plot, a compliance code, a diagnostic code, a test code, an alarm, and a rating value.

8. A method for evaluating iontophoretic delivery devices, the method comprising:
applying at least a first test signal to an iontophoresis delivery device being evaluated;
measuring at least one resistive or capacitive response of the iontophoresis delivery device being evaluated to at least the first test signal;
comparing at least a first value indicative of the measured at least one resistive or capacitive response of the iontophoresis delivery device to one or more reference data sets indicative of at least one resistive or capacitive response of at least one reference iontophoresis delivery device; and
determining whether the iontophoresis delivery device being evaluated meets an acceptance criteria based at least in part on the comparison, wherein applying at least a first test signal to an iontophoresis delivery device being evaluated includes applying a first alternating current of a first frequency to the iontophoretic delivery device being evaluated at a first time and applying a second alternating current of a second frequency to the iontophoretic delivery device being evaluated at a second time, the second frequency different than the first frequency.

9. The method of claim 8 wherein measuring at least one resistive or capacitive response of the iontophoresis delivery device being evaluated includes measuring at least one of a magnitude or a phase shift of a response signal to each of the first and the second alternating currents with an impedance spectrometer.

10. A system for evaluating iontophoresis devices, comprising:
an impedance spectrometer operable to measure an impedance of an iontophoresis device;
a database comprising stored iontophoresis device reference data;
a controller configured to perform a comparison of the measured impedance of the iontophoresis device to the stored reference data, and to generate a response based in part on the comparison, wherein the impedance spectrometer includes at least one frequency response analyzer (FRA), and is configured to determine the impedance of the iontophoresis device for at least two selected frequencies of an alternating current.

11. The system of claim 10, further comprising:
at least one potentiostat/galvanostat.

12. The system of claim 10 wherein the iontophoresis device takes the form of an iontophoretic drug delivery patch.

13. The system of claim 10, further comprising:
a test interface, communicatively coupled to the impedance spectrometer and selectively positionable with respect to the iontophoresis device being evaluated to make electrical contact with at least two portions of the iontophoresis device being evaluated.

14. The system of claim 13 wherein the test interface includes four electrodes and is operable to perform a four-point impedance measurement.

15. The system of claim 10 wherein the response comprises at least one of a comparison plot, a compliance code, a diagnostic code, a test code, an alarm, and a rating value.

16. A system for evaluating iontophoresis devices, comprising:
an impedance spectrometer operable to measure an impedance of an iontophoresis device;
a database comprising stored iontophoresis device reference data;
a controller configured to perform a comparison of the measured impedance of the iontophoresis device to the stored reference data, and to generate a response based in part on the comparison, wherein the stored reference data comprises impedance data, characteristic phase delay data, characteristic amplitude data, characteristic resistance data, characteristic electrolyte resistance data, characteristic interface capacitance data, and characteristic ionic movement data.

17. The system of claim 16 wherein the characteristic phase delay data comprises phase delay data at two or more frequencies of an alternating current; and the characteristic amplitude data comprises amplitude data at two or more frequencies of the alternating current.

18. The system of claim 16 wherein the characteristic phase delay data comprises one or more phase delay ranges; and the characteristic amplitude data comprises one or more amplitude ranges.

* * * * *